United States Patent
Baermann et al.

(10) Patent No.: US 6,780,150 B2
(45) Date of Patent: *Aug. 24, 2004

(54) THERAPEUTIC SPIRAL MAGNET

(75) Inventors: Horst M. Baermann, Berg. Gladbach (DE); Horst Geissler, Pulheim (DE)

(73) Assignee: Baermann Magnetics, Inc., Spartenburg, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 10/410,157

(22) Filed: Apr. 10, 2003

(65) Prior Publication Data

US 2003/0195381 A1 Oct. 16, 2003

Related U.S. Application Data

(63) Continuation of application No. 09/518,262, filed on Mar. 3, 2000, now Pat. No. 6,558,310.

(51) Int. Cl.⁷ ................................................ A61N 1/00
(52) U.S. Cl. .............................................. 600/9; 600/15
(58) Field of Search ........................................ 600/9–15

(56) References Cited

U.S. PATENT DOCUMENTS

| | | |
|---|---|---|
| 5,017,185 A | 5/1991 | Baermann |
| 5,450,858 A | 9/1995 | Zablotsky et al. |
| 5,514,072 A | 5/1996 | Ardizzone |
| 5,538,495 A | 7/1996 | Ardizzone |
| 4,549,532 A | 8/1998 | Baermann |
| 5,984,856 A | 11/1999 | Love |
| 6,126,589 A | 10/2000 | Brooks |
| 6,558,310 B1 * | 5/2003 | Baermann et al. ............ 600/9 |

FOREIGN PATENT DOCUMENTS

| | | |
|---|---|---|
| DE | 33 31 061 A | 3/1985 |
| DE | 37 30 077 A | 4/1988 |
| DE | 37 19 306 A | 12/1988 |
| DE | 94 12 807.3 | 10/1994 |
| EP | 0 198 958 A | 10/1986 |
| GB | 2 205 999 A | 12/1988 |
| GB | 2 294 120 A | 4/1996 |
| WO | WO 93 13720 A | 7/1993 |

* cited by examiner

*Primary Examiner*—John P. Lacyk
(74) *Attorney, Agent, or Firm*—Nixon & Vanderhye, P.C.

(57) ABSTRACT

Magnet spirals for therapeutic application with a minimum one foil strip made of a rubber-type flexible, preferably skin compatible, plastic which is coiled up along its lengthwise dimension in the form of a spiral, whereby the foil strip is magnetically polarized in an axial (perpendicular) direction relative to its longer lateral faces prior to coiling. The longer lateral faces of the foil strip are magnetically polarized in an axial direction of the foil—that is, in the thickness direction of the foil strip, preferably up to its total saturation. In the coiled condition of the foil, one side of the lateral area thus faces the other side of the lateral area. Starting at the center, this configuration creates, in a radial direction, a sequence of varying magnetic polarizations within the cross section of the magnet spiral. The effect of this series arrangement of the magnetic polarizations causes the creation of a particularly strong magnetic field in the vicinity of the magnet spiral. The strength of the magnetic field is caused in particular by a multitude of magnetic dipoles being arranged in series along their magnetic axes. In the case of the magnet spiral according to the present invention, the foil strip may be coiled up around itself, or around an object of optional form in the center of the spiral. The magnet spiral of the present invention may, for example, have a largely circular form circumference, or a rectangular periphery with rounded-off corners or irregularly shaped.

3 Claims, 7 Drawing Sheets

THERAPEUTIC SPIRAL MAGNET

This is a continuation of application Ser. No. 09/518,262, filed Mar. 3, 2000, now U.S. Pat. No. 6,558,310.

FIELD OF THE INVENTION

The present invention relates generally to spiral magnets. More specifically, the present invention relates to devices comprising spiral magnets which are usefully employed for therapeutic applications.

BACKGROUND AND SUMMARY OF THE INVENTION

The use of magnetic fields for therapeutic application is well known. For example, U.S. Pat. No. 4,549,532 to Baermann (the entire content of which is expessly incorporated hereinto by reference) discloses a flexible magnetic foil for therapeutic purposes. Primarily, the therapeutic action is produced by the Hall effect, which causes a load separation within an electrolyte which flows through the magnetic field. Electric voltages are thereby created diagonally to the flow direction, which can generate the desired therapeutic action in the sections of the body thus treated.

Such devices for therapeutic application are typically manufactured using foils made of a rubber-type flexible plastic, which is preferably skin-compatible. Permanently magnetic particles are embedded in the plastic, which are preferably permanently magnetic particles of a ferrite or rare-earth component, for example such as barium or strontium ferrite, or NdFeB. These permanently magnetic particles are aligned by applying an external magnetic field to one, or both, side(s) of the foil and thus create a magnetically polarized area. The conventional foil is thus a sheet-type formation, with a commonly available foil thickness of between 0.3 mm and 1.5 mm.

Various designs of such conentional magnetic foils are known. They are made by stamping or cutting from commonly available magnetic foils, normally in the form of circular discs or rectangles. Double or multi-polar magnetization is usually carried out laterally on one side. The pole configurations thereby are usually in the form of straight lines, concentric circles, spirals, rectangles, or sections, as well as other geometric formations. Only in the case of axial magnetization, whereby one surface has a single N-pole and the reverse side of the foil a single S-pole, are identical magnetic induction values shown at corresponding measuring points on both sides.

In contrast to a double sided lateral multi-polar magnetization, the afore-mentioned single-sided lateral multi-polar magnetization has the advantage that it is normally very practical and shows higher induction values on the side of the foil adjacent to the patient's body than it would exhibit in the case of two-sided lateral polarization with the identical pole configuration, irrespective of the configuration.

However, the above dual or multi-polar lateral magnetizations of such sheet-type formations are unfavorable due to the magnetic flux direction being curved within large sections of the foil. The desired total saturation polarization of the overal available magnetic material, on the utilization side of the foil facing the body, can thus no longer be ensured.

This problem proves to be of particular disadvantage for magnetic foils used for therapeutic purposes, where the pole width is larger than the foil thickness. However, magnetizing with pole widths which are in excess of the 1-time, often even 20-times, that of the foil thickness are preferred due to their desired greater dispersion into deeper areas of the body. An additional disadvantage of this type of magnetization has proven to be the leakage flux which forms on the reverse side of the foil, due to the low relative permeability of $\mu r=1.0$. This may be as much as 75% of the area of the foil facing the body and reduces the desired beneficial flow considerably.

In some cases however, this disadvantage is compensated by the side of the foil facing the body being covered by a magnetic, highly permeable foil, for example of thin low-carbon steel sheeting. Due to this magnetic reflux, the utilization flux of the foil is highly increased. A disadvantage however, is the use of steel sheeting which, due to its negligible thickness, presents a considerable injury potential. Its use increases the manufacturing price and also reduces the flexibility of the foil.

Therefore, in summary, the use of such magnetic therapeutic devices is limited by the strength of the polarization. With a weak polarization of the foil used, the effect produced by the magnetic field within the body, is also weak.

The present invention invention is based on the purpose of providing a magnetic device for therapeutic application which may be easily manufactured and which generates a strong and effective magnetic field.

By this invention, the above purpose is accomplished by a magnet spiral for therapeutic application with minimum one foil strip made of a rubber-type flexible, preferably skin compatible, plastic which is coiled up along its lengthwise dimension in form of a spiral, whereby the foil strip is magnetically polarized in an axial direction relative to its larger lateral face (i.e. in its lengthwise direction).

Preferably, the magnet spiral according to the present invention includes a minimum of one magnetically polarized foil strip which is coiled up into a spiral. Thereby, the larger lateral faces of the foil are magnetically polarized in an axial direction of the foil—that is, in the lengthwise direction of the foil strip, preferably up to its total saturation. The axial direction refers to the foil in its coiled condition. In the coiled condition of the foil, one side of the larger lateral area thus faces the other large lateral area. Starting at the center this configuration creates in a radial direction a sequence of varying magnetic polarizations within the cross section of the magnet spiral. The effect of this series arrangement of the magnetic polarizations causes the creation of a particularly strong magnetic field in the vicinity of the magnet spiral. The strength of the magnetic field is caused in particular by a multitude of magnetic dipoles being arranged in series along their magnetic axes.

In the case of the magnet spiral according to the present invention, the foil strip may be coiled up around itself, or around an object of optional form in the center of the spiral. The magnet spiral of the present inveniton invention may, for example, have a largely circular form circumference, or a rectangular periphery with rounded-off corners, or irregularly shaped.

In preferred embodiments, the foil has the form of an enlongated strip with right angled cross section, whereby powder-type magnetic components, preferably Sr-ferrite or NdFeB of particle size smaller than 1 mm, particularly preferable smaller than 100$\mu$, are embedded in as evenly formed statistical dispersion as possible. In the case of such a strip, the larger lateral faces are those faces, which run in the longitudinal direction of the strip and which are broader. A strip-type foil is particularly easy to coil. For the manufacture of a magnet spiral according to the present invention, it is useful for the practical application to positionally fix the free end of the strip, in the coiled-up condition, to the magnet spiral. This may be achieved, for example, by using an adhesive strip or a similar fixing method.

In another preferred embodiment of the invention, a minimum of two different polarizations are applied to each of the large lateral faces, whereby the polarization is in each case set in opposition. Thereby, beside the magnetic effect caused by the axial polarization of the foil, a further source for the magnetic field is created due to the additional magnetic polarization on the larger lateral face, which acts similarly to a dipole arranged across the axial direction of the foil. The field distribution of the magnet spiral can thereby be favorably modified.

Several areas of varying polarization may follow on the one side, along the lengthwise extent of the foil's coil. With a series arrangement of varying polarization areas on the one side, along the lengthwise direction, two areas of identical polarization become adjacent to one another in one section of the coiled foil. Whereas, in the case of identical polarization of the large side areas, two varying polarizations always abutt, so that in the cross-section of the magnet spiral North pole and South pole of a dipole always abutt. In the case of a different polarization on the large side areas, a North pole of one foil section—in the cross-section of the magnet spiral—abutts at least once to a North pole of another following foil element, lying in the winding direction. With reference to the magnetization of the spiral, three ring shaped poles of the magnet spiral are created in the area in which, for example, two regions of identical polarization meet. When such a meeting of identical polarization occurs, the magnet spiral largely shows a rotation symmetric polarization which occurs in radial direction, for example with a North-pole, South-pole and North pole again. The pole sequence is caused by two foil elements for example, being aligned contrary to one another, whereby North-pole abutts North-pole. Such a magnetic field, with more poles, may also be favorable for therapeutic application, since the change of the magnetic fields has additional and particularly favored effect on electrolytes in the vicinity of the field.

In one useful form, the areas following one another in the longitudional direction of the foil's winding, represent a length of a minimum angle zone of $2\pi$ radians each. Thereby it is ensured that a fundamental rotation-symmetric field distribution is created.

Preferably the spiral is in the form of an essentially cylindrical configuration, with the cylinder height being smaller than the cylinder diameter. A magnet spiral so dimensioned is easy to handle.

The objective of the invention is also accomplished by a device for therapeutic application, particularly a bandage, pocket and face mask, which contains at minimum one of the above described spirals. A minimum of one foil, coiled up into a spiral, is arranged in a device for therapeutic application. Therefore, bandages, pockets and face masks are suitable. The device is worn with its effective surface as close as possible to the body part which is intended to be treated and is in need fo the magnetic thereapy.

In a further embodiment of the invention, a minimum of two foils, each coiled in the shape of a spiral and set with a space between them is intended. Thereby, similar to a Helmholtz coil pair, a magnetic field can be created between the two spirals. Such a magnetic field may be particularly favourable for a therapeutic application of the device. Also, the individual foils coiled into spirals may be arranged in the device in such a way that very specific field configurations are created, insofar as this is desired for a therapeutic action.

In a preferred implementation of the invention, a minimum of two foils, each coiled in the shape of a frontal spiral, are intended to be arranged essentially with spiral axes falling on top of one another, with a space between them. Thereby, for example, a minimum of two alternating magnetic poles are created, between which the part of the body to be treated may be arranged.

Favourably, the front of the spiral is arranged in the vicinity of the body part to be treated. An advantage of such a spiral arrangement is that there is a very strong magnetic field along the effective area of the device. Therefore for example, the spiral may be arranged inside a bandage or a pocket parallel to the skin.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein;

FIGS. 1A–1C each schematically represent exemplary geometric forms of a therapeutic spiral magnet in accordance with the present invention;

FIG. 2 schematically shows a magnetic foil which is magnetized in its thickness direction;

FIG. 3 schematically shows a magnetic foil with several areas of varying polarization following one another;

Figure 4:
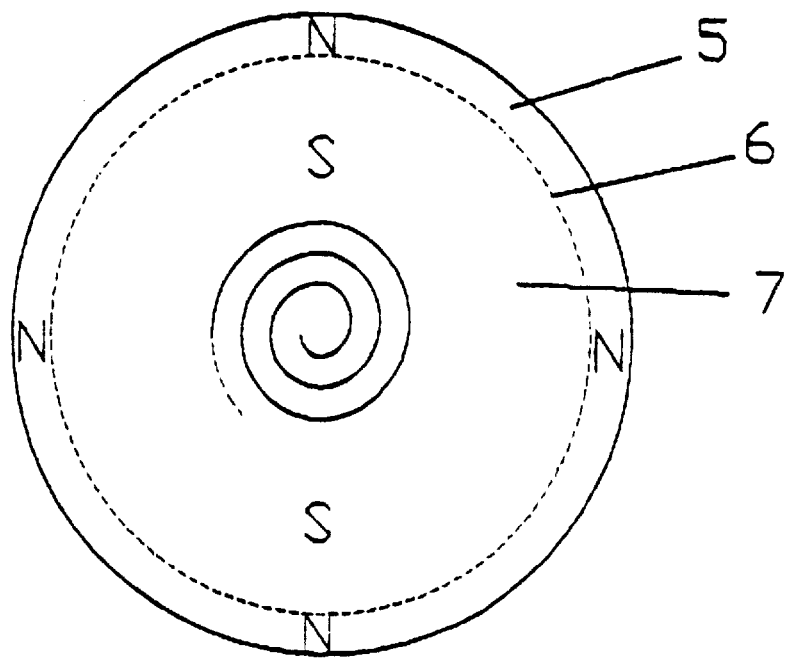
FIG. 4 shows an exemplary magnet spiral with an externally positioned North-pole and an internally positioned South-pole made from a magnetic foil as in FIG. 2.
Figure 6:
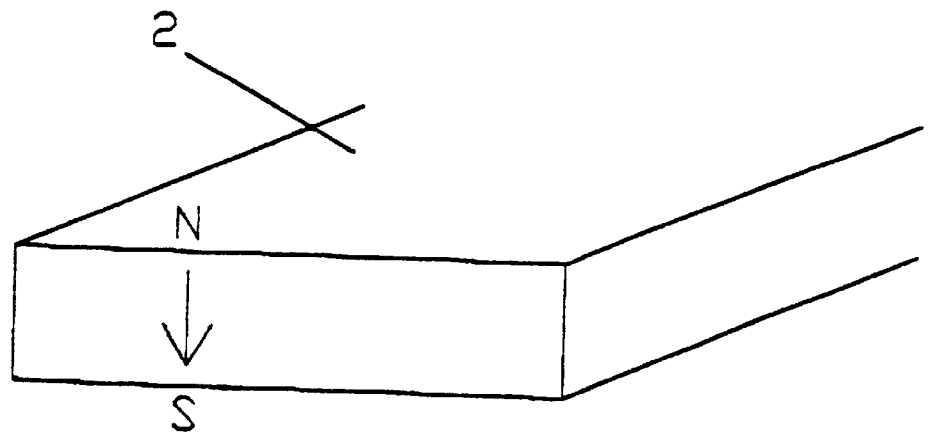
Figure 7A:
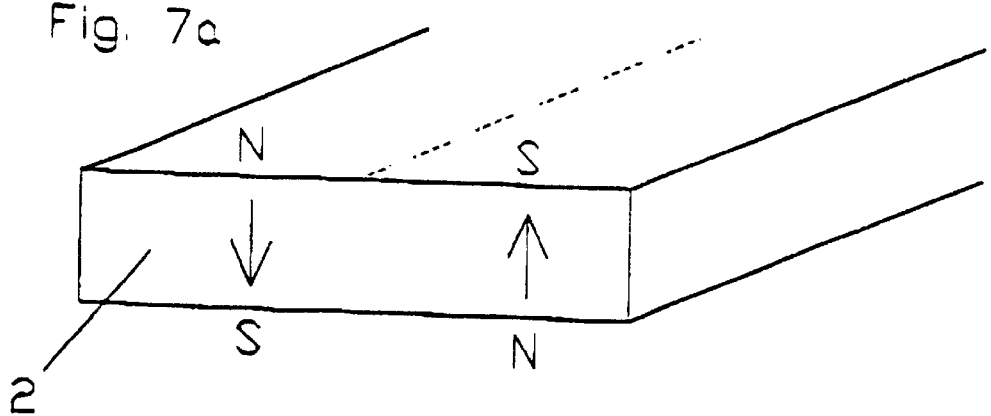
Figure 7B:
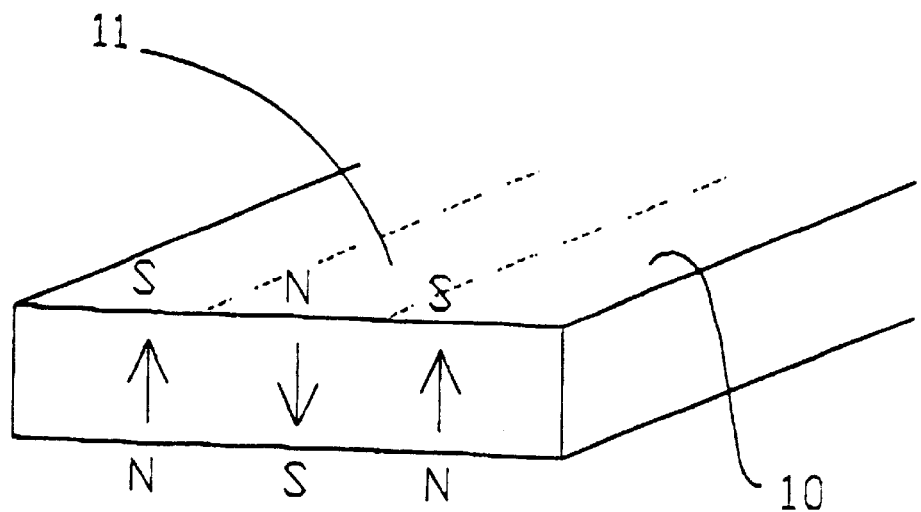
Figure 8:
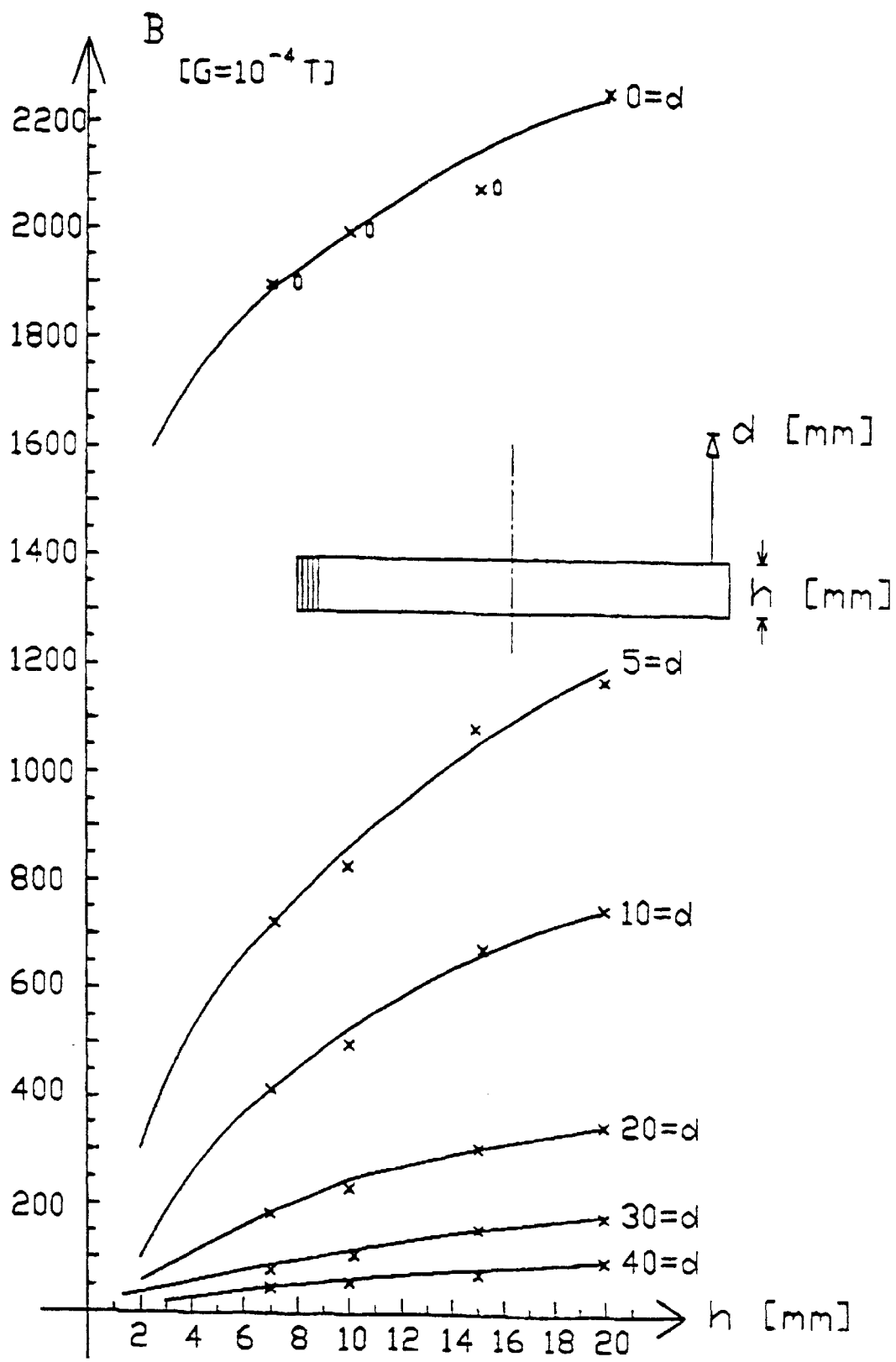
Figures 9, 10:
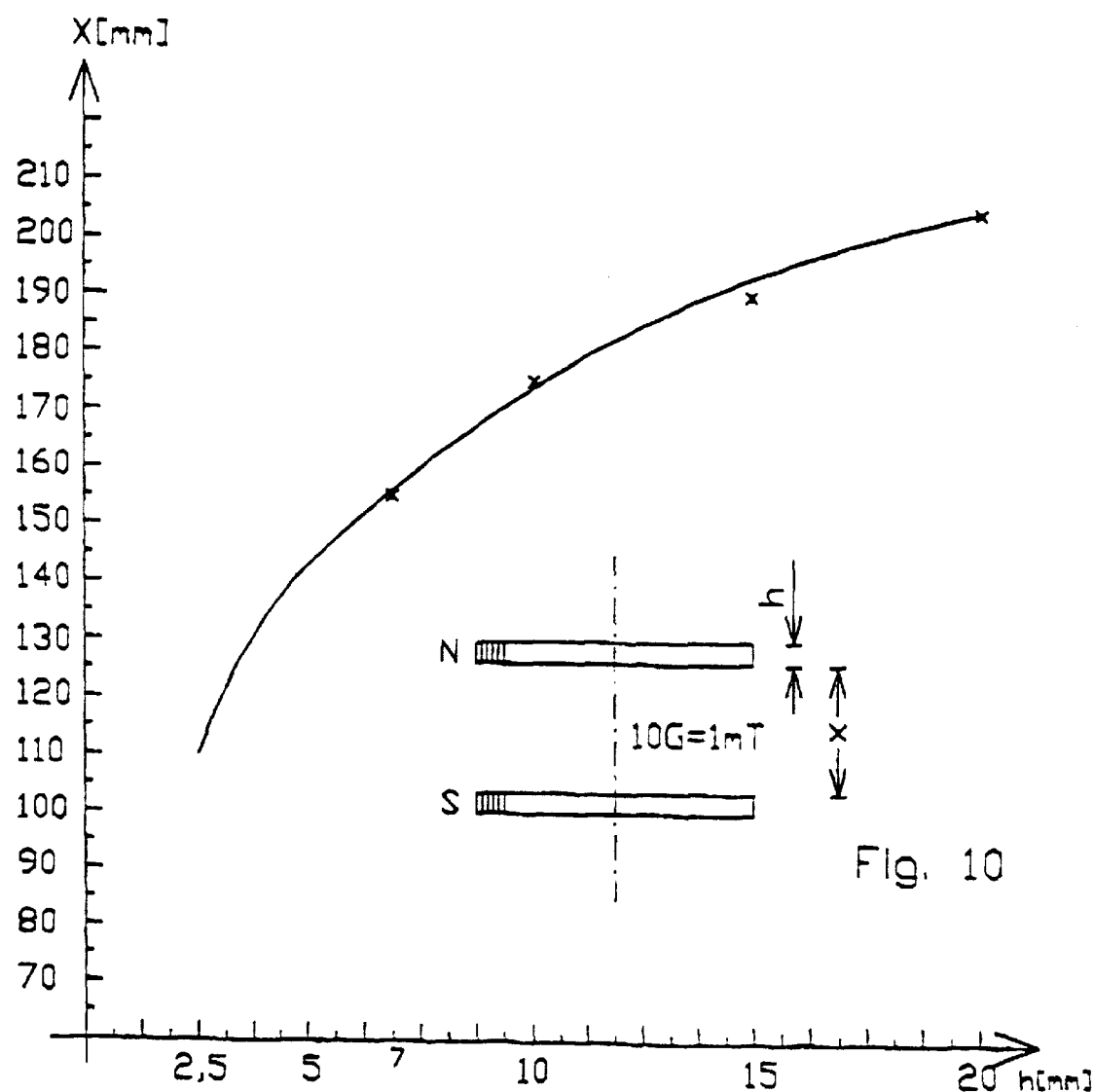
Figure 11:
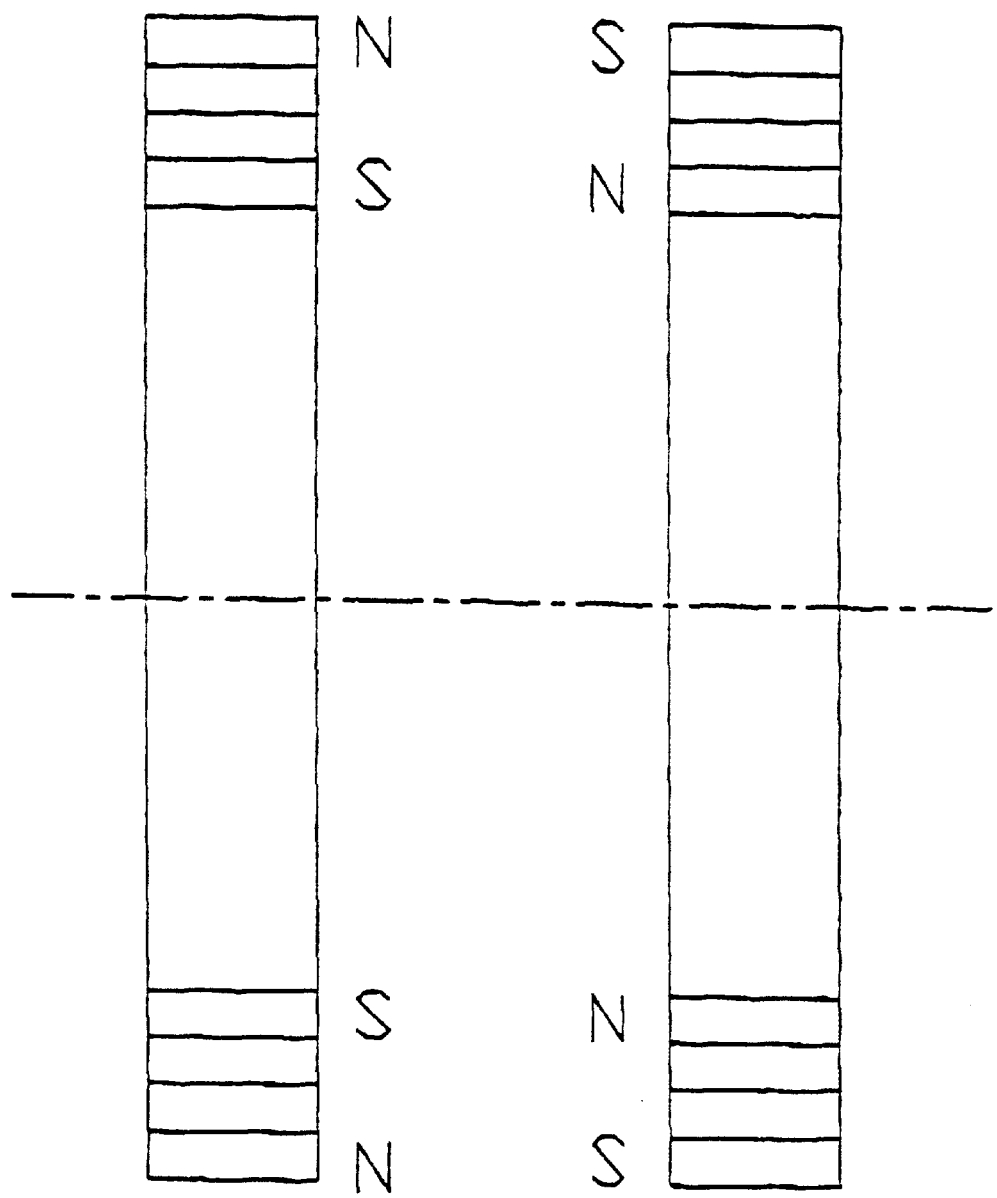

FIG. 6 schematically depicts a magnetic foil with axial polarization on the larger lateral face area;

FIG. 7A shows a magnetic foil with two varying polarizations on the larger lateral face area;

FIG. 7B a magnetic foil with several varying polarizations on the larger lateral face area;

FIG. 8 is a graphical plot of induction values on a magnet spiral dependent on thickness and spacing measured with a magnet as shown in FIG. 4;

FIG. 9 is a graphical plot of measurements of the spacing of two magnet spirals arranged axially to one another as in FIG. 4, the poles of which are polarized contrary to one another, at constant field strength inside the center of the arrangement;

FIG. 10 schematically depicts the arrangement of the magnet spirals for measuring the spacing at constant field strength as per FIG. 9; and FIG. 11 schematically depicts a pair of magnet spirals in cross-section, which are arranged coaxially and spaced from one another with contrary poles.

DETAILED DESCRIPTION OF THE INVENTION

Figure 1A:
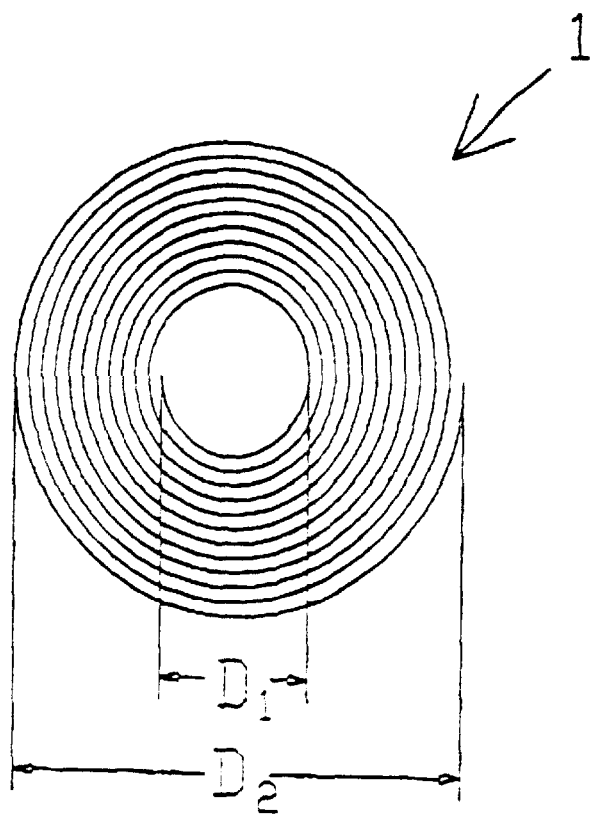

One form of a magnet spiral 1 in accordance with the present invention is depicted in accompanying FIG. 1A. Specifically, the magnet spiral 1 is formed by a foil strip being coiled up to have a substantially circular shaped circumference. The spiral 1 shown in FIG. 1A thus has an internal diameter D1 and an external diameter D2, it being understood that the magent spiral 1 also has a height dimension not shown extending into the plane of FIG. 1A. As a result, a basically circular shaped internal area of diameter D1 remains free in the center of magnet spiral 1 in which objects may be placed. The sizes of some exemplary magnet spirals may be, for example, D1=3 mm, D2=40 mm, height: 2.5 mm; D1=5 mm, D2=150 mm, height: 15 mm; D1=50 mm, D2=150 mm, height: 30 mm.

Figure 1B:
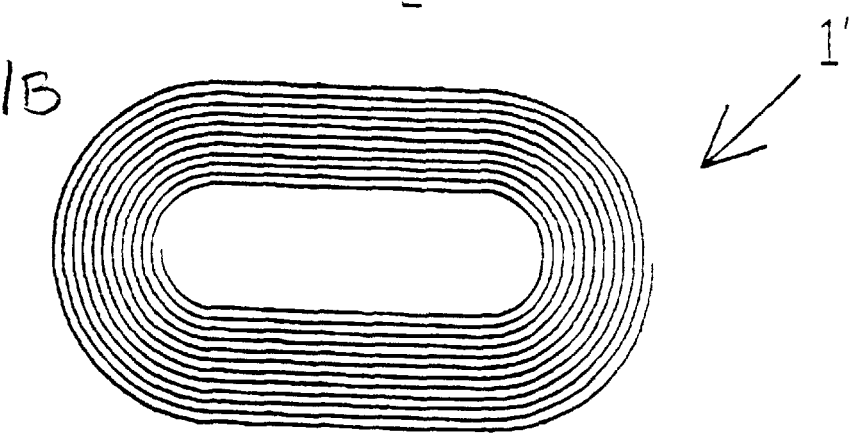
Figure 1C:
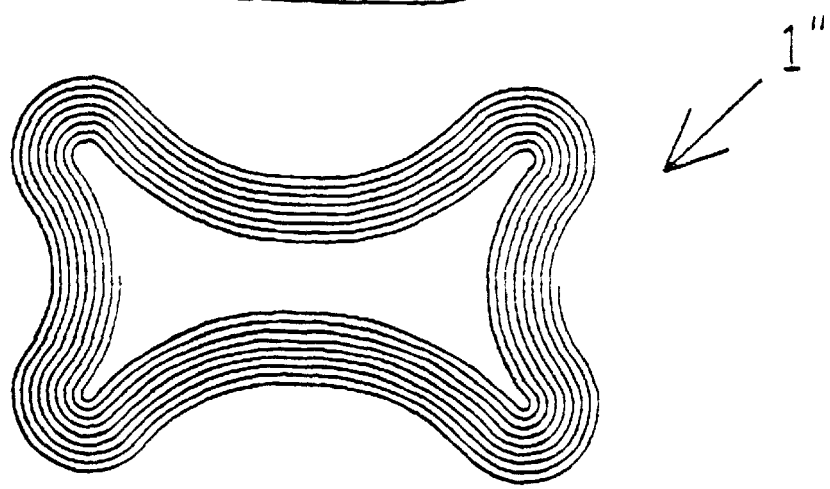

The circular shaped spiral 1 shown in FIG. 1A is exemplary only. Thus, the magnet spiral may thus take the form of a generally rectangular circumference with rounded off corners by winding the foil around a square object as shown by magnet spiral 1' in FIG. 1B. Alternatively, the magnet spiral 1" shown in FIG. 1C may be formed into an irregular circumferential shape.

Figure 2:
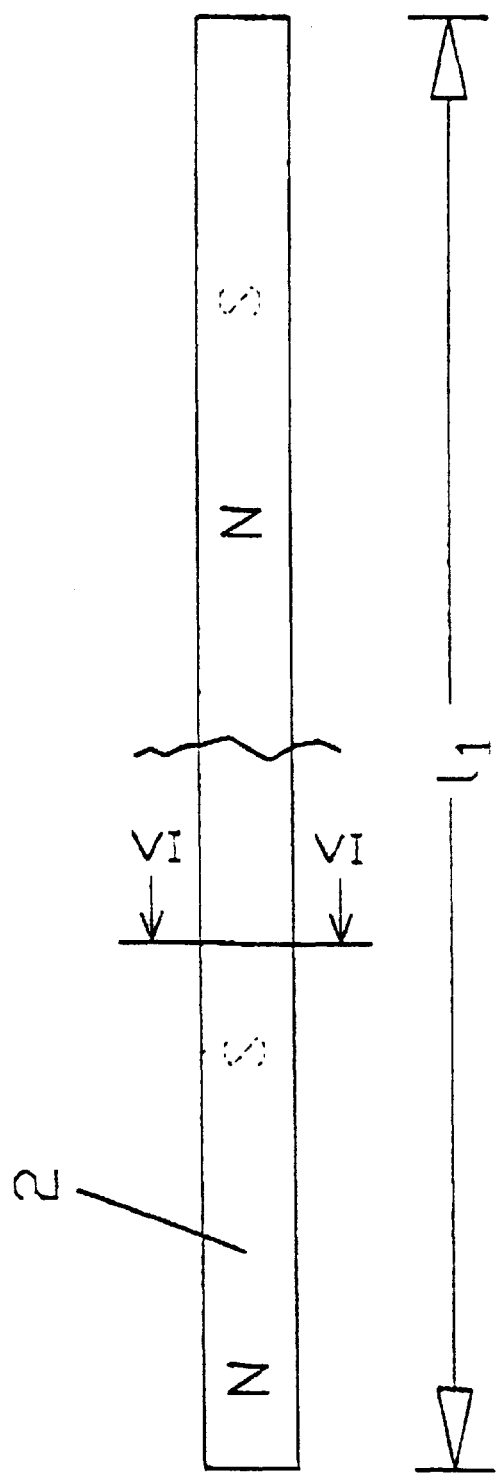

The foil strips from which the magnet spiral is formed by coiling most preferably exhibits a consistent magnetic polarization in the direction of its thickness as shown in FIG. 2. The foil strip has the length L1 and may be coiled up along its length.

As an annex on the first coiled-up foil strip, further foil strips may be wound around the first foil thereby enveloping the same. The polarization of the larger side face area of the second foil strip, which is wound around the first foil, may be the same as, or opposite to, the polarization of the first foils larger side face area. Such a series winding of several foil strips acts on the magnetic field of the magnet spiral like a consistent or alternating polarization in the longitudinal direction when using exactly one foil.

Accompanying FIG. 2 shows that the reverse side (i.e., with the pole letter identifier being dotted) of a magnetized foil strip has the opposite polarization. The foil strip shown in FIG. 2 is therefore axially polarized which is also clarified by FIG. 6, showing a cross section through a foil strip.

Figure 3:
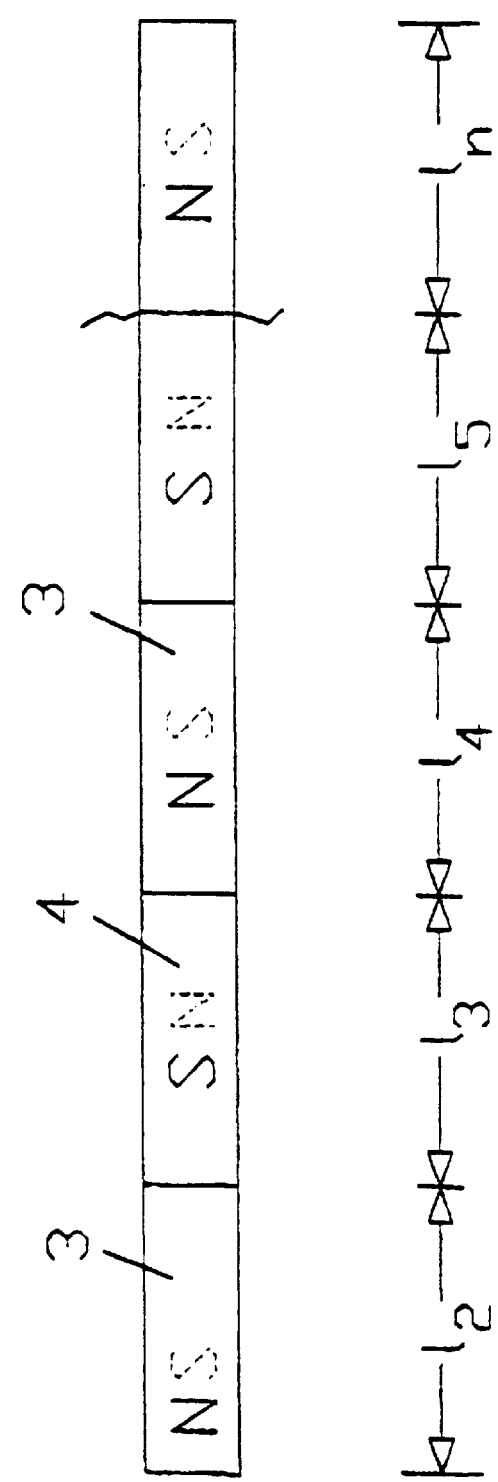

In the case of the foil strip shown in FIG. 3, areas 3 and 4 are alternately abutted with one another with respectively different polarizations on the larger side face areas. Area 3 thus has a length L2 and the area 4 a length L3. The lengths L2, L3 are such that, in a coiled-up condition of the foil, each length has made at least one winding circumferentially. That is, the areas 3, 4 serially following one another in the longitudional direction of the foil's winding, each represent a length of a minimum angle zone of $2\pi$ radians each. As a result, it is ensured that a fundamental rotation-symmetric field distribution is created.

When foil strip 2 of FIG. 2 is coiled up, a magnet spiral is created which has two poles on its facing side. If the side face area of foil strip 2, which is magnetized with a South pole, faces inwards, the pole distribution of the magnet spiral shown in FIG. 4 is created. A magnetic North pole 5 is arranged in the peripheral area of the magnet spiral and a magnetic South pole 7 in the central area of the magnet spiral. A separating line 6 runs along the intermediate area which identifies, simultaneously, a neutral zone and the transition between the magnetic poles 5 and 7.

Figure 5:
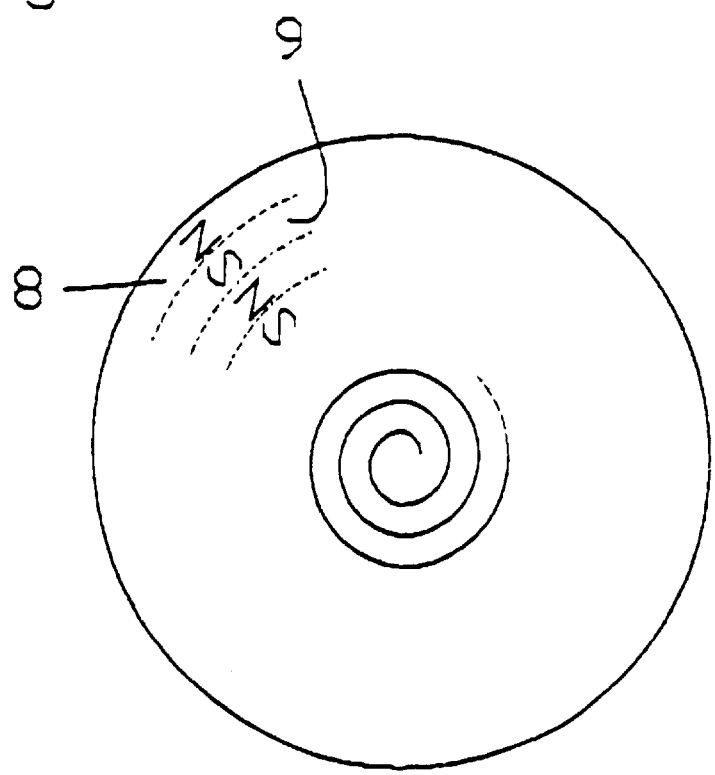
FIG. 5 shows an exemplary spiral magnet with an alternating radial pole sequence made from the magnetic foil depicted in FIG. 3.

If, as shown in FIG. 3, several varying magnetic polarized areas are arranged in series, a pole distribution as shown in FIG. 5 may be created. Thereby, magnetic North pole 8 and magnetic South pole 9 alternate with each other from one winding to the next.

It is also possible to apply several areas of magnetic polarization to the large side faces of the foil. Thus, FIG. 6 shows a cross section of the magnetic foil described in FIG. 2 with a common polarization 2 on the larger side faces. The foil shown in FIG. 6 is axially magnetized, because North and South poles lie opposite to one another on the large side faces of the foil strip.

FIGS. 7a and 7b each respectively show axially magnetized foil strips, whereby several areas of alternately varied magnetization are arranged side-by-side on the large side face. In FIG. 7b, for example, area 10 is arranged at the edge of the foil and is adjacent to a central area 11 with opposite polarization.

An example of the operating mode of a magnet spiral is explained by reference to FIGS. 8–10. In this regard, as shown graphically in FIG. 8, the magnetic flux density of a magnet spiral is dependent upon its height 'h' and the spacing 'd' at the indicated measurement point. One can see from FIG. 8 therefore that the magnetic induction increases when the magnet spiral's height 'h' increases.

From the measurements shown in FIG. 8 it can also be gathered that the strength of the magnetic flux density decreases with increasing distance 'd' from the surface of the magnet spiral. Each distance 'd' is hereby indicated in mm. The measured values show roughly a four to tenfold strength when using an identical magnetic component, in comparison to using an uncoiled magnetic foil strip. This represents a considerable advantage of the effect of the magnet spiral.

FIG. 9 shows the dependency of spacing 'X' of two magnet spirals, with opposite polarity and being arranged parallel to one another, on the height of these spirals, whereby the magnetic induction in the center between both magnet spirals, coiled up as per FIG. 4, is 1 mT=10 Gauβ. Such an arrangement is shown in FIG. 10.

This arrangement explains that in the space area between two magnet spirals, being arranged parallel to one another on the frontal side, a considerably strong and thereby effective magnetic flux density can be obtained which is suitable for a therapeutic utilization. Such an arrangement of the spirals may be used beneficially, for example, in knee, back, hip, arm, and elbow bandages, whereby this invention shows that the high induction values obtained when the distances between the surfaces of the magnet spirals are identical, represent a particular advantage.

A further advantageous arrangement of two magnet spirals is shown in FIG. 11 in cross-section. In this case, two magnet spirals are located opposite to one another in such a way that in each case two opposite poles face one another. By way of such an arrangement of the magnet spirals particularly high induction values are obtained in the volume contained between the magnet spirals, which is of particular advantage for the therapeutic treatment of body parts arranged in this area.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A magnetic spiral device for therapeutic application comprising at least one flexible foil strip:

having a length and a width that define a first side face, having said length and an axial depth that define a second side face that adjacently faces a patient's body, wherein the foil strip is magnetically polarized in an axial depth direction prior to coiling the foil strip into a spiral pattern, wherein the foil strip is coiled along its first side face, and wherein the coiled foil strip is configured for subsequent therapeutic magnetic effect in a lateral direction to the patient's body.

2. The device according to claim 1 wherein at least one of said device is contained in a bandage.

3. The device according to claim 1 wherein at least one of said device is contained in a pocket.

* * * * *